United States Patent
Matsumoto

(10) Patent No.: US 11,574,189 B2
(45) Date of Patent: Feb. 7, 2023

(54) IMAGE PROCESSING APPARATUS AND LEARNED MODEL

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 468 days.

(21) Appl. No.: 16/819,158

(22) Filed: Mar. 15, 2020

(65) Prior Publication Data

US 2020/0218980 A1 Jul. 9, 2020

Related U.S. Application Data

(63) Continuation of application No. PCT/JP2018/033399, filed on Sep. 10, 2018.

(30) Foreign Application Priority Data

Oct. 6, 2017 (JP) .............................. JP2017-196350

(51) Int. Cl.
| | |
|---|---|
| *G06V 10/774* | (2022.01) |
| *G06N 3/04* | (2006.01) |
| *G06T 7/00* | (2017.01) |
| *G06V 10/772* | (2022.01) |
| *A61B 1/045* | (2006.01) |
| *G06N 3/08* | (2006.01) |

(Continued)

(52) U.S. Cl.
CPC ............... *G06N 3/08* (2013.01); *G06N 20/00* (2019.01); *G06V 10/25* (2022.01)

(58) Field of Classification Search
CPC ...................................................... G06V 10/25
See application file for complete search history.

(56) References Cited

U.S. PATENT DOCUMENTS

| | | | |
|---|---|---|---|
| 2013/0222540 A1* | 8/2013 | Tajima | H04N 13/261 |
| | | | 348/43 |
| 2015/0086110 A1 | 3/2015 | Nishimura et al. | |
| 2018/0011953 A1* | 1/2018 | Micks | G06F 30/20 |

(Continued)

FOREIGN PATENT DOCUMENTS

| | | |
|---|---|---|
| JP | H04125779 | 4/1992 |
| JP | H0836643 | 2/1996 |

(Continued)

OTHER PUBLICATIONS

"International Search Report (Form PCT/ISA/210)" of PCT/JP2018/033399, dated Nov. 20, 2018, with English translation thereof, pp. 1-8.

(Continued)

*Primary Examiner* — Hsiungfei Peng
(74) *Attorney, Agent, or Firm* — JCIPRNET

(57) ABSTRACT

An image processing apparatus having a processor configured to: select a reference frame from a frame group including a plurality of images; acquire a reference correct answer frame representing a region of interest in the selected reference frame; generate a complementary correct answer frame corresponding to a frame other than the reference frame included in the frame group based on at least one reference correct answer frame; and generate a correct answer image group for machine learning from the reference correct answer frame and the complementary correct answer frame.

20 Claims, 5 Drawing Sheets

(51) Int. Cl.
 *G06N 20/00* (2019.01)
 *G06V 10/25* (2022.01)

(56) References Cited

U.S. PATENT DOCUMENTS

2018/0322346 A1* 11/2018 Davies ................... G06F 16/95
2020/0286290 A1*  9/2020 Averianov ............... G06T 7/38

FOREIGN PATENT DOCUMENTS

| JP | 2013242825 | 12/2013 |
| JP | 2017074363 | 4/2017 |
| WO | 2016136214 | 9/2016 |

OTHER PUBLICATIONS

"Written Opinion of the International Searching Authority (Form PCT/ISA/237)" of PCT/JP2018/033399, dated Nov. 20, 2018, with English translation thereof, pp. 1-7.

* cited by examiner

IMAGE PROCESSING APPARATUS AND LEARNED MODEL

CROSS-REFERENCE TO RELATED APPLICATIONS

This application is a Continuation of PCT International Application No. PCT/JP2018/033399 filed on Sep. 10, 2018, which claims priority under 35 U.S.C § 119(a) to Japanese Patent Application No. 2017-196350 filed on Oct. 6, 2017. Each of the above applications is hereby expressly incorporated by reference, in its entirety, into the present application.

BACKGROUND OF THE INVENTION

1. Field of the Invention

The present invention relates to an image processing apparatus that creates a correct answer image group used in machine learning, and a learned model that is generated by performing machine learning using the correct answer image group created by the image processing apparatus.

2. Description of the Related Art

In the medical field, image diagnosis in which a doctor performs diagnosis by interpreting an image obtained by an imaging apparatus such as an X-ray CT apparatus or MRI has been performed. In order to assist the image diagnosis, a diagnosis assistance apparatus that assists discovery of a lesion region in the image has been suggested (for example, refer to JP2017-074363A).

In this type of diagnosis assistance apparatus, in order to generate accurate assistance information by an inference unit including a neural network circuit, it is necessary for the inference unit to perform machine learning on a feature of the lesion region using multiple correct answer images (training data) (for example, refer to JP1996-036643A (JP-H8-036643A) and JP1992-125779A (JP-H4-125779A)).

SUMMARY OF THE INVENTION

The correct answer images used in machine learning are generally created by hand. In order to create the correct answer images, a work such as a masking process is performed by designating the lesion region for each frame included in a frame group of a plurality of images. Thus, in a case where the number of frames included in the frame group is enormous, a lot of effort is necessary for performing the work in order to create the correct answer images.

The present invention is conceived in view of the above matter. An object of the present invention is to provide an image processing apparatus and a learned model capable of efficiently creating a correct answer image group to be used in machine learning from a frame group of a plurality of images.

An image processing apparatus according to one aspect of the present invention is an image processing apparatus that creates a correct answer image group to be used in machine learning from a frame group of a plurality of images, comprising a reference frame selection unit that selects a specific reference frame from the frame group, a reference correct answer frame acquisition unit that acquires a reference correct answer frame representing a region of interest in the selected reference frame, and a complementary correct answer frame creation unit that creates a complementary correct answer frame corresponding to a frame other than the reference frame included in the frame group based on at least one reference correct answer frame acquired by the reference correct answer frame acquisition unit.

A learned model according to one aspect of the present invention is generated by performing machine learning using a correct answer image group created by the image processing apparatus.

According to the present invention, an image processing apparatus capable of efficiently creating a correct answer image group to be used in machine learning from a frame group of a plurality of images can be provided.

In addition, according to the present invention, a learned model can be generated by performing machine learning using a correct answer image group created from a frame group of a plurality of images.

DESCRIPTION OF THE PREFERRED EMBODIMENTS

Hereinafter, an embodiment of the present invention will be described in detail with reference to the drawings.

Figure 1:
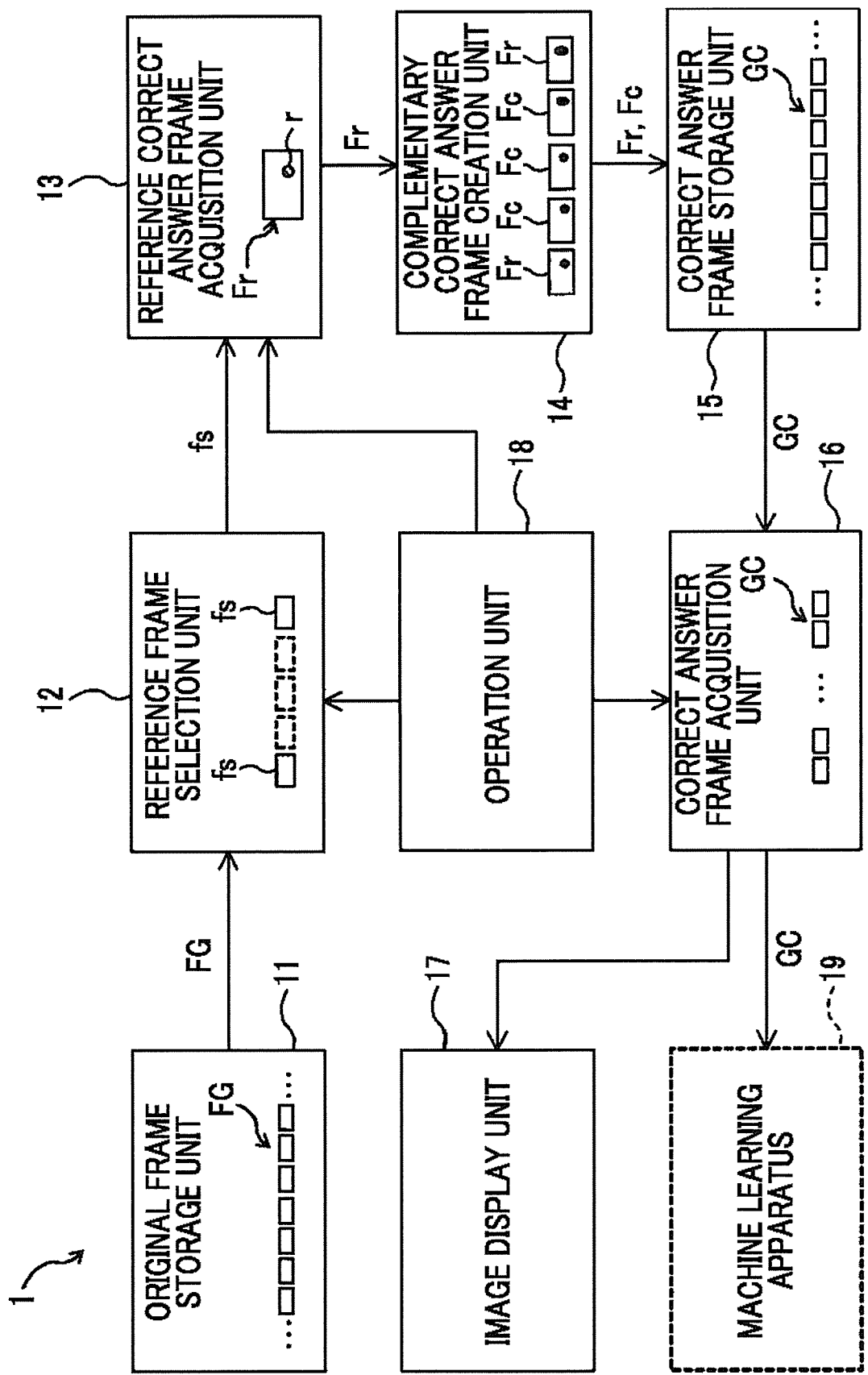
FIG. 1 is a block diagram illustrating a configuration of an image processing apparatus according to one embodiment of the present invention.

FIG. 1 is a block diagram illustrating a configuration of an image processing apparatus according to one embodiment of the present invention. An image processing apparatus 1 illustrated in FIG. 1 includes an original frame storage unit 11, a reference frame selection unit 12, a reference correct answer frame acquisition unit 13, a complementary correct answer frame creation unit 14, a correct answer frame storage unit 15, a correct answer frame acquisition unit 16, an image display unit 17, and an operation unit 18.

A hardware configuration of the image processing apparatus 1 is implemented by a processor performing various processes by executing a program, a random access memory (RAM), and a read only memory (ROM). The processor includes a central processing unit (CPU) that is a general-purpose processor performing various processes by executing a program, a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute a specific process, or the like. More specifically, structures of these various processors are electric circuits in which circuit elements such as semiconductor elements are combined. In addition, a processor constituting an evaluation system may be configured with one of the various processors or may be configured with a combination (for example, a combination of a plurality of FPGAs or a combination of a CPU and an FPGA) of two or more processors of the same type or different types.

The original frame storage unit 11 stores data of a frame group FG that constitutes a motion picture obtained by imaging performed by an endoscope apparatus or the like. The frame group FG is not limited to the motion picture and may be a frame group of a plurality of images having a time series relationship or a frame group of a plurality of images simply forming an aggregate.

The reference frame selection unit 12 selects one or a plurality of specific reference frames fs satisfying a predetermined condition from the frame group FG stored in the original frame storage unit 11. The reference frame selection unit 12 may present a plurality of frames satisfying the predetermined condition as candidates and select a frame designated from the operation unit 18 as the reference frame fs.

The predetermined condition that is a reference in a case of selecting the reference frame fs is that an image of the frame has a small amount of shake or blurriness and a value indicating a degree of blurriness or shake is less than or equal to a threshold value. In a case of using a single frame, for example, the degree of shake or blurriness can be quantified by performing image analysis or frequency analysis on an edge intensity or a contrast of the image. In a case of using a plurality of frames, the degree of shake or blurriness can be quantified by analyzing a velocity vector of deviation amounts, directions, or the like.

Regarding shake, the degree of shake can be calculated for each frame from data detected at a time of imaging by a gyroscope or an acceleration sensor mounted in the endoscope apparatus or the like. Regarding blurriness, the degree of blurriness can be calculated for each frame from data such as a depth of focus in the endoscope apparatus or the like. By embedding the value indicating each of the calculated degrees of shake and blurriness in the image of each frame as reference information, or by managing the value in association with identification information (ID) of each frame, the reference frame selection unit 12 can refer to the value indicating each of the degrees of shake and blurriness in a case of selecting the reference frame fs. In addition, a frame for which the value indicating each of the degrees of shake and blurriness is less than or equal to a threshold value, and a frame for which the value is greater than the threshold value may be stored in different folders in the original frame storage unit 11. In this case, the reference frame selection unit 12 may select the reference frame fs from the folder in which the frame for which the value is less than or equal to the threshold value is stored.

In a case of a captured image of the endoscope apparatus, not only the image having shake or blurriness but also an image in which cleaning water is applied throughout the image, an image in which a residue and residual liquid are present, and an image in which a treatment tool is captured in the frame may be determined as not satisfying the predetermined condition. Accordingly, a frame not satisfying the predetermined condition may be specified by detecting presence of an object blocking an observation target using an image feature such as the edge intensity or a contour shape. In this case, sorting such as storing the frame in a different folder as a frame not selected as the reference frame fs may be performed in advance by specifying the frame based on an acquisition time of the frame not satisfying the predetermined condition or test information associated with the acquisition time of the frame.

The reference correct answer frame acquisition unit 13 acquires a reference correct answer frame Fr that represents a region of interest r in the reference frame fs. The reference correct answer frame Fr may be created by causing the reference correct answer frame acquisition unit 13 to specify the region of interest r and perform image processing on the region of interest r based on an operation input from the operation unit 18. Alternatively, data of the reference frame fs may be output to a system different from the image processing apparatus 1 of the present embodiment, and the reference correct answer frame acquisition unit 13 may acquire the data in which the different system specifies the region of interest r and performs the image processing on the region of interest r from the different system. For example, the region of interest r is a region that includes a lesion part in the image captured by the endoscope apparatus. In addition, for example, the image processing performed on the region of interest r is a masking process (filling process).

The complementary correct answer frame creation unit 14 creates a complementary correct answer frame Fc corresponding to a frame other than the reference frame fs included in the frame group FG based on at least one reference correct answer frame Fr acquired by the reference correct answer frame acquisition unit 13. The complementary correct answer frame creation unit 14 may create the complementary correct answer frame Fc from the frame other than the reference frame fs based on the reference correct answer frame Fr.

In a case where the reference frame selection unit 12 selects a plurality of reference frames fs and the reference correct answer frame acquisition unit 13 acquires a plurality of reference correct answer frames Fr based on each reference frame fs, the complementary correct answer frame creation unit 14 creates the complementary correct answer frame Fc by assigning an image obtained by performing a morphing process based on images of the region of interests r of two reference correct answer frames Fr to an intermediate frame constituting the motion picture between the two reference correct answer frames Fr. The image obtained by the morphing process is assigned to a region corresponding to the region of interest r in each image of the intermediate frame. Thus, even in a case where coordinate positions of the region of interests r in the two reference correct answer frames Fr are different from each other, the image is assigned to an appropriate coordinate position in the intermediate frame.

In a case where the reference frame selection unit 12 selects one reference frame fs, the complementary correct answer frame creation unit 14 creates the complementary correct answer frame Fc by creating an image based on at least one of a shape model or a shape change model from one reference correct answer frame Fr acquired by the reference correct answer frame acquisition unit 13 and assigning the image to a frame after the reference correct answer frame Fr. The shape model is a model that approximates a lesion region or the like in the frame to an ellipse or the like. The shape change model is a model that changes a shape of the ellipse or the like approximated to the lesion region or the like in the frame using a time function based on a dynamic contour model. Any of the models approximates or defines the shape of the lesion region or the like to be learned by machine learning as a function in advance. The shape of the lesion region or the like is not limited to the ellipse and may be approximated by a two-dimensionally representable polygon or a circle or the like or a combination thereof. The shape change model complies with a rule of a shape change based on time such that in a closed region configured with N vertexes (control points) and N−1 edges, any number and positions of control points are moved by any distance at a time based on time among the N control points. This rule may be statistically decided by machine learning or may be experimentally approximated or defined by a person without machine learning.

The correct answer frame storage unit 15 stores data of a correct answer frame group GC that is a correct answer image group configured with the reference correct answer frame Fr acquired by the reference correct answer frame acquisition unit 13 and the complementary correct answer frame Fc created by the complementary correct answer frame creation unit 14. A correct answer frame constituting the correct answer frame group GC is not limited to the frame and may be, for example, coordinate information that represents the region of interest r and can be converted into the correct answer frame.

The correct answer frame acquisition unit 16 acquires data of all or a part of the frames from the correct answer frame group GC stored in the correct answer frame storage unit 15 depending on an instruction from the operation unit 18. The data of the frame acquired by the correct answer frame acquisition unit 16 is transmitted to a machine learning apparatus 19 or the image display unit 17 depending on a content of the instruction from the operation unit 18.

The image display unit 17 displays images of the frame group FG constituting the motion picture, an image of the reference correct answer frame Fr, or images of the correct answer frame group GC. In addition, the image display unit 17 displays an operation menu and a button icon and the like that are referred to in a case where a user of the image processing apparatus 1 operates the operation unit 18.

The operation unit 18 is means for the user of the image processing apparatus 1 to perform various operations. Specifically, the operation unit 18 is a trackpad, a touch panel, a mouse, or the like.

Next, a method of creating the correct answer frame group GC which is the correct answer image group by the image processing apparatus 1 of the present embodiment will be described with reference to the flowchart illustrated in FIG. 2.

Figure 2:
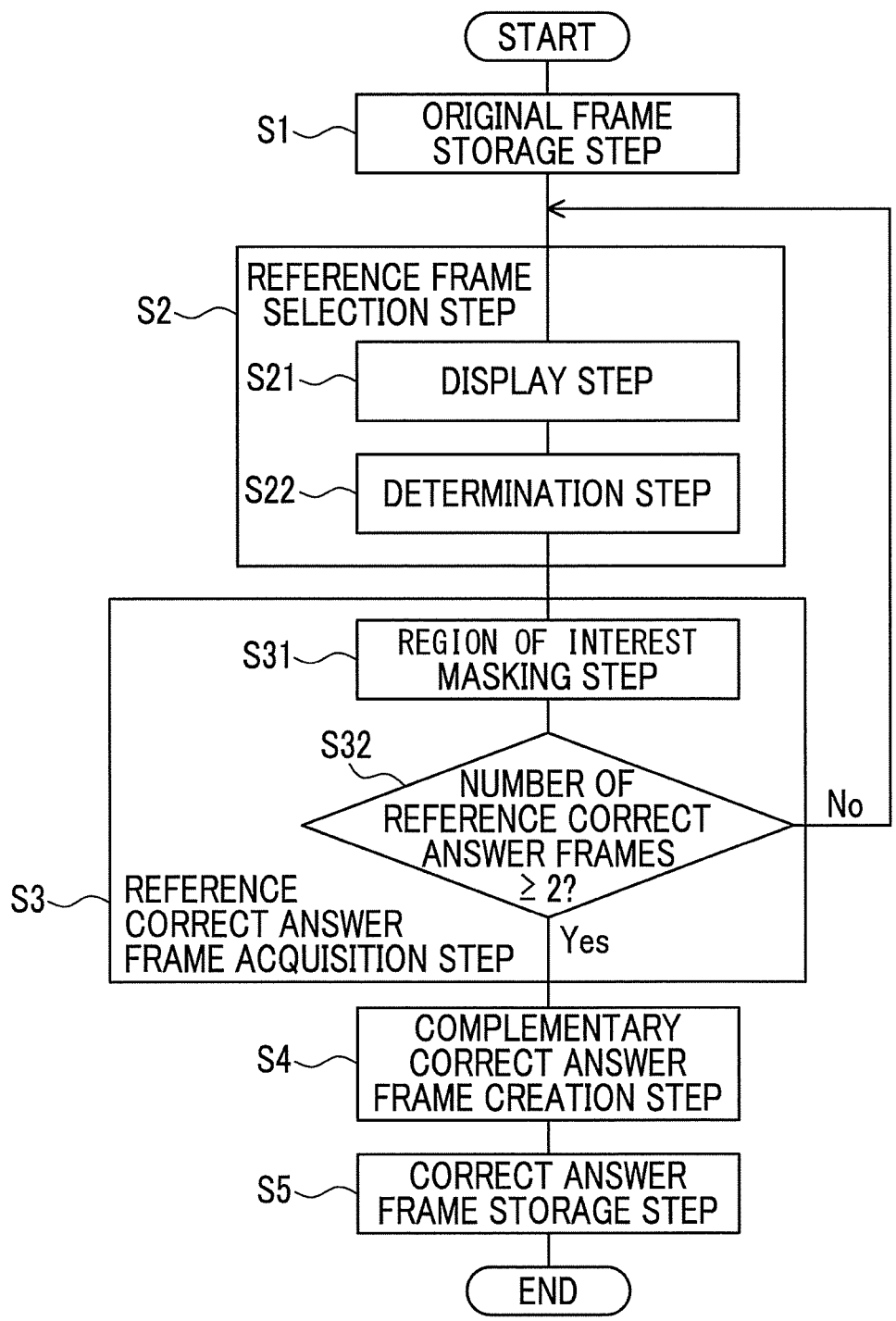
FIG. 2 is a flowchart illustrating a correct answer image creation method according to the embodiment of the present invention.

Processes executed by the flowchart illustrated in FIG. 2 include original frame storage step S1, reference frame selection step S2, reference correct answer frame acquisition step S3, complementary correct answer frame creation step S4, and correct answer frame storage step S5.

Figure 3A:
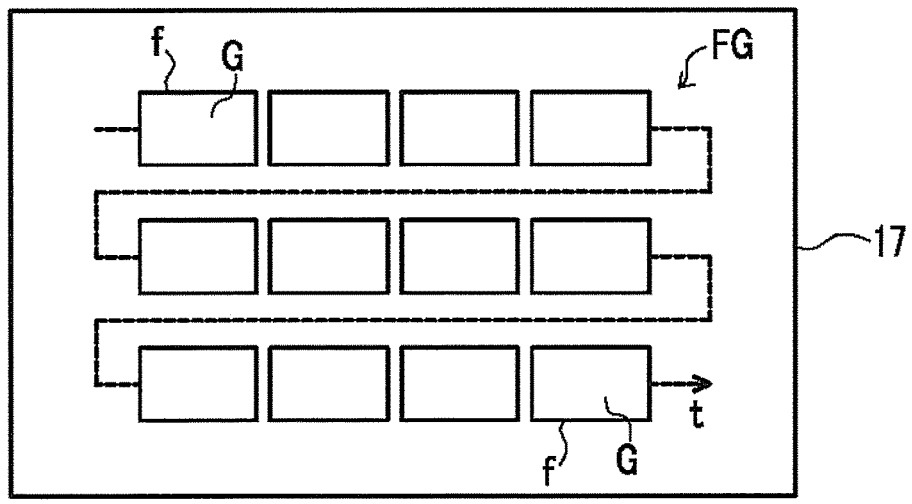
FIG. 3A is a descriptive diagram of a display form of a frame group constituting a motion picture.

In original frame storage step S1, the data of the frame group FG constituting the motion picture obtained by imaging performed by the endoscope apparatus or the like is stored in the original frame storage unit 11. The frame group FG stored in the original frame storage unit 11 is displayed on the image display unit 17 as illustrated in FIG. 3A. In the example illustrated in FIG. 3A, an image G of each frame f constituting the frame group FG is displayed in order along a time axis t.

Figure 3B:
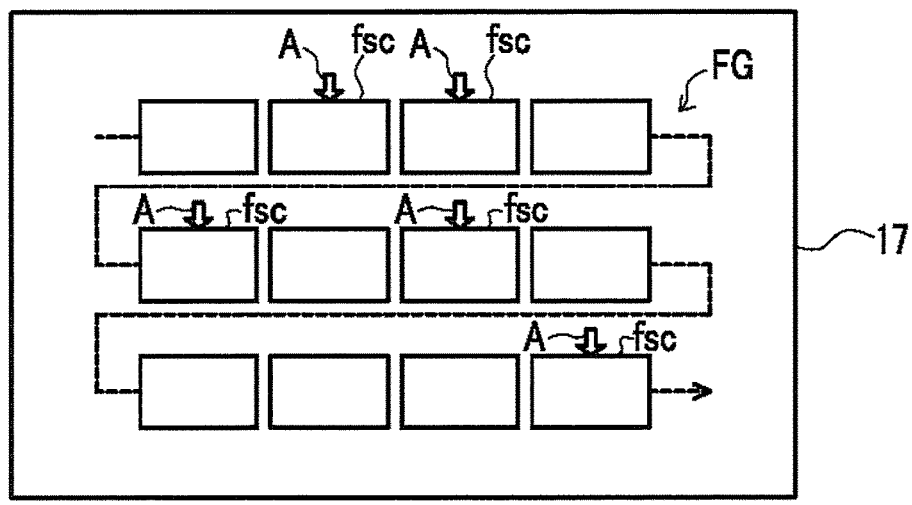
FIG. 3B is a descriptive diagram of a display form of candidates of a reference frame.

In reference frame selection step S2, the reference frame selection unit 12 selects one or a plurality of specific reference frames fs satisfying the predetermined condition from the frame group FG stored in the original frame storage unit 11. In the present embodiment, candidates (hereinafter, referred to as "candidate frames") fsc of the reference frame fs are selected by the reference frame selection unit 12 and are presented on the image display unit 17 as illustrated in FIG. 3B. In the example illustrated in FIG. 3B, a plurality of candidate frames fsc are presented in a form of indicating the plurality of candidate frames fsc by arrow A. Alternatively, the plurality of candidate frames fsc may be presented in a form of displaying frame numbers.

Figure 3C:
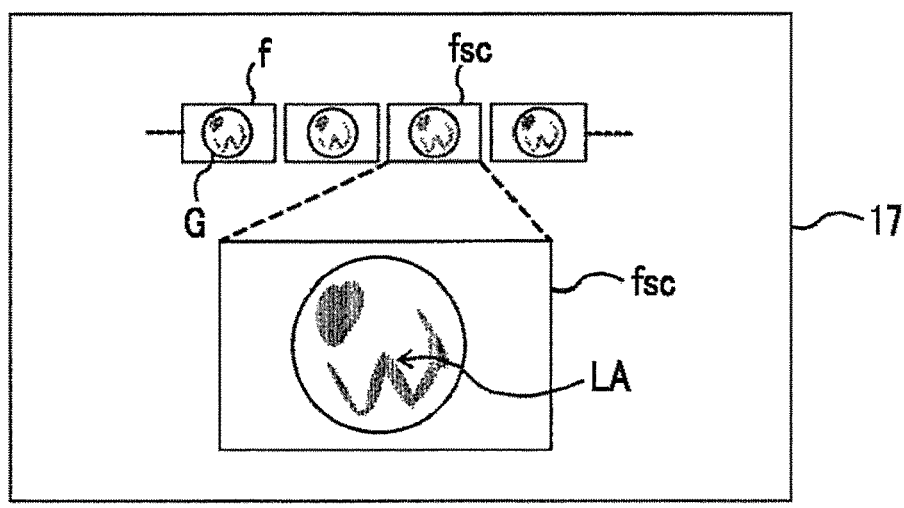
FIG. 3C is a descriptive diagram illustrating a state where any candidate frame is displayed in an enlarged manner.

Reference frame selection step S2 includes display step S21 of displaying each candidate frame fsc in an enlarged manner and determination step S22 of determining whether or not the candidate frame fsc displayed in an enlarged manner is a clear image not having blurriness or shake. In display step S21, the user of the image processing apparatus 1 displays any candidate frame fsc on the image display unit 17 in an enlarged manner as illustrated in FIG. 3C. Next, in determination step S22, the user of the image processing apparatus 1 determines whether or not, particularly, a lesion part LA of the candidate frame fsc displayed in an enlarged manner is clearly captured without blurriness or shake. In a case where the user of the image processing apparatus 1 selects the reference frame fs from the candidate frames fsc, a transition is made to reference correct answer frame acquisition step S3.

In reference correct answer frame acquisition step S3, the reference correct answer frame acquisition unit 13 acquires the reference correct answer frame Fr representing the region of interest r in the reference frame fs. Reference correct answer frame acquisition step S3 includes region of interest masking step S31 and reference correct answer frame number determination step S32.

Figure 4:
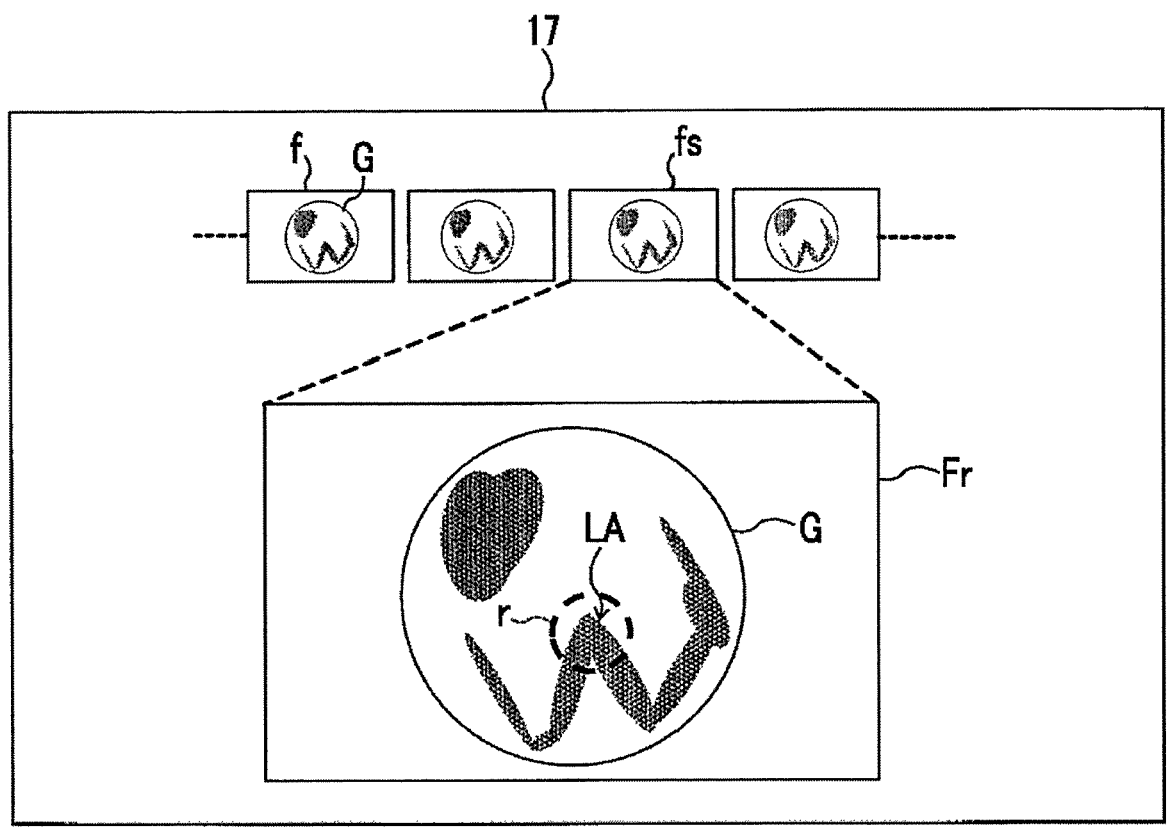
FIG. 4 is a descriptive diagram of creation of a reference correct answer frame.

In region of interest masking step S31, as illustrated in FIG. 4, the user of the image processing apparatus 1 specifies the region of interest r including the lesion part LA in the image G by operating the operation unit 18 while viewing the image G of the reference frame fs displayed on the image display unit 17, and performs the image processing (masking process) on the region of interest r. In region of interest masking step S31, the reference correct answer frame acquisition unit 13 acquires the reference correct answer frame Fr by creating the reference correct answer frame Fr from the reference frame fs. In reference correct answer frame number determination step S32, a determination as to whether or not two or more reference correct answer frames Fr are acquired is performed. In a case where it is not determined that two or more reference correct answer frames Fr are acquired (No in step S32), a return is made to reference frame selection step S2. In a case where it is determined that two or more reference correct answer frames Fr are acquired (Yes in step S32), a transition is made to complementary correct answer frame creation step S4.

Figure 5:
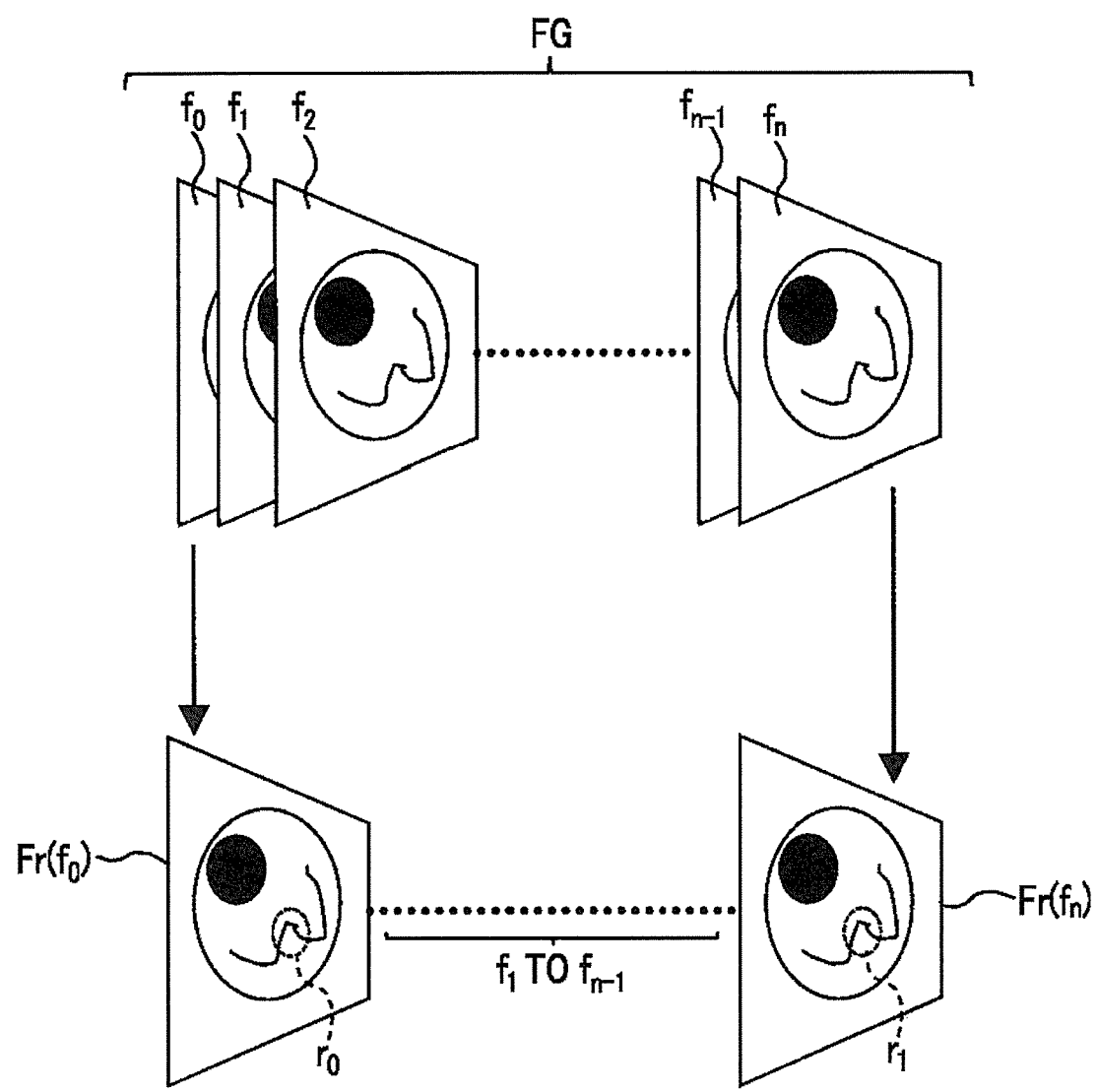
FIG. 5 is a descriptive diagram of creation of a correct answer image group from an original frame group.

In complementary correct answer frame creation step S4, the complementary correct answer frame creation unit 14 creates the complementary correct answer frame Fc by performing the morphing process based on the images of the region of interests r of the two reference correct answer frames Fr acquired in reference correct answer frame acquisition step S3 and assigning the image obtained by the morphing process to the intermediate frame constituting the motion picture between the two reference correct answer frames Fr. In the example illustrated in FIG. 5, two frames $f_0$ and $f_n$ at both ends of the frame group FG including a plurality of frames $f_0$ to $f_n$ are selected as the reference frame fs, and the two reference correct answer frames Fr are created. The data of the frame group FG including the reference correct answer frames Fr ($f_0$ and $f_n$) is input into the complementary correct answer frame creation unit 14. The complementary correct answer frame creation unit 14 creates the complementary correct answer frame Fc by performing the morphing process based on images of region of interests $r_0$ and $r_n$ of the two reference correct answer frames Fr ($f_0$ and $f_n$) and assigning the image obtained by the morphing process to the intermediate frames $f_1$ to $f_{n-1}$ constituting the motion picture between the two reference correct answer frames Fr ($f_0$ and $f_n$).

Next, in correct answer frame storage step S5, the complementary correct answer frame creation unit 14 stores the reference correct answer frame Fr acquired in reference correct answer frame acquisition step S3 and the complementary correct answer frame Fc created in complementary correct answer frame creation step S4 in the correct answer frame storage unit 15. The correct answer frame storage unit 15 stores the correct answer frame group GC which is the correct answer image group configured with the reference correct answer frame Fr and the complementary correct answer frame Fc.

Data of the whole or a part of the correct answer frame group GC stored in the correct answer frame storage unit 15 is read by the correct answer frame acquisition unit 16 and is transmitted to the machine learning apparatus 19 or the image display unit 17. The data transmitted to the machine learning apparatus 19 is used as learning data of machine learning performed by the machine learning apparatus 19. The machine learning apparatus 19 generates a learned model by performing the machine learning. The generated learned model has a configuration of a convolutional neural network and is used in the evaluation system of the lesion part included in the image acquired by the endoscope apparatus.

The machine learning apparatus 19 includes a processor performing the machine learning, a random access memory (RAM), and a read only memory (ROM). The evaluation system includes a processor performing various processes by executing the learned model as a program, a RAM, and a ROM. The processor includes a central processing unit (CPU) that is a general-purpose processor performing various processes by executing a program, a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute a specific process, or the like. More specifically, structures of these various processors are electric circuits in which circuit elements such as semiconductor elements are combined. In addition, the processor constituting the evaluation system may be configured with one of the various processors or may be configured with a combination (for example, a combination of a plurality of FPGAs or a combination of a CPU and an FPGA) of two or more processors of the same type or different types.

According to the configuration of the present embodiment described above, the correct answer frame group GC which is the correct answer image group configured with the reference correct answer frame Fr and the complementary correct answer frame Fc is created by selecting at least one (in the example in FIG. 5, two of the frame $f_0$ and the frame $f_n$) frame in which the lesion part LA is clearly captured from the frame group FG constituting the motion picture obtained by imaging performed by the endoscope apparatus or the like, acquiring the reference correct answer frame Fr by specifying the region of interest r of each selected frame and performing the image processing, and creating the complementary correct answer frame Fc based on the reference correct answer frame Fr. In addition, the learned model can be generated by using the data of the whole or a part of the created correct answer frame group GC as the learning data of the machine learning. The learned model is used in the evaluation system of the lesion part included in the image acquired by the endoscope apparatus. While the learned model generally means a function that is represented as a combination of a structure of a neural network and a parameter (so-called "weight") that is strength of a connection between neurons constituting the neural network, the learned model in the present specification means a program for performing an operation process based on the function.

The present invention is not limited to the embodiment, and modifications, improvements, and the like can be appropriately made. For example, in the embodiment, in reference frame selection step S2, the candidate frames fsc satisfying the predetermined condition are presented, and the candidate frame fsc selected from the candidate frames fsc by the user of the image processing apparatus 1 using the operation unit 18 is selected as the reference frame fs by the reference frame selection unit 12. Alternatively, the reference frame selection unit 12 may select one or a plurality of frames satisfying the predetermined condition as the reference frame fs without presenting the candidate frames fsc.

In the embodiment, in reference correct answer frame acquisition step S3, the reference correct answer frame Fr is acquired by causing the user of the image processing apparatus 1 to specify the region of interest including the lesion part in the image by operating the operation unit 18 while viewing the image of the reference frame fs displayed on the image display unit 17, and performing the image processing (masking process) on the region of interest. Alternatively, the data of the reference frame fs may be output to a system different from the image processing apparatus 1, and the data in which the different system specifies the region of interest and performs the image processing on the region of interest may be input into the image processing apparatus 1 and be acquired as the reference correct answer frame Fr.

In the embodiment, in complementary correct answer frame creation step S4, the morphing process is performed as a frame complementation method of the intermediate frame constituting the motion picture between the two reference correct answer frames Fr. Alternatively, other frame complementation methods may be employed. For example, in a case where only one reference correct answer frame Fr is present, the complementary correct answer frame Fc may be created by creating an image based on at least one of the shape model or the shape change model from the reference correct answer frame Fr and assigning the image to a frame after the reference correct answer frame Fr.

As described thus far, an image processing apparatus disclosed in the present specification is an image processing apparatus that creates a correct answer image group to be used in machine learning from a frame group of a plurality of images, comprising a reference frame selection unit that selects a specific reference frame from the frame group, a reference correct answer frame acquisition unit that acquires a reference correct answer frame representing a region of interest in the selected reference frame, and a complementary correct answer frame creation unit that creates a complementary correct answer frame corresponding to a frame other than the reference frame included in the frame group based on at least one reference correct answer frame acquired by the reference correct answer frame acquisition unit.

The reference frame selection unit selects the reference frame based on a result of analysis of images of frames included in the frame group.

The frame group includes a plurality of frames in time series.

The reference frame selection unit selects the reference frame based on a degree of shake or blurriness of an image of each frame constituting the frame group.

The reference frame selection unit quantifies the degree of shake or blurriness by performing image analysis or frequency analysis on a single frame.

The reference frame selection unit quantifies the degree of shake or blurriness by analyzing a velocity vector of deviation amounts or directions of a plurality of frames.

The reference frame selection unit selects the reference frame based on a result of detection of an image feature of each frame constituting the frame group.

The reference frame selection unit selects the reference frame based on data that is detected by a gyroscope or an acceleration sensor in a case of imaging each frame of the frame group.

The image processing apparatus further comprises an operation unit for performing an operation of designating any frame from the frame group or an operation for performing image processing on the designated frame, in which the reference correct answer frame acquisition unit creates the reference correct answer frame by specifying the region of interest and performing the image processing on the region of interest based on an operation input from the operation unit.

In a case where the reference frame selection unit selects a plurality of the reference frames, the complementary correct answer frame creation unit creates the complementary correct answer frame by assigning an image obtained by performing a morphing process based on images of the region of interests of two reference correct answer frames acquired by the reference correct answer frame acquisition unit to an intermediate frame constituting a motion picture between the two correct answer reference frames.

A learned model disclosed in the present specification is generated by performing machine learning using a correct answer image group created by the image processing apparatus.

The learned model has a configuration of a convolutional neural network.

EXPLANATION OF REFERENCES

1: image processing apparatus
11: original frame storage unit
12: reference frame selection unit
13: reference correct answer frame acquisition unit
14: complementary correct answer frame creation unit
15: correct answer frame storage unit
16: correct answer frame acquisition unit
17: image display unit
18: operation unit
19: machine learning apparatus
$f_0$ to $f_n$: frame
Fc: complementary correct answer frame
FG: frame group
Fr: reference correct answer frame
fs: reference frame
fsc: candidate frame
G: image
GC: correct answer frame group
LA: lesion part
r: region of interest
S1: original frame storage step
S2: reference frame selection step
S3: reference correct answer frame acquisition step
S4: complementary correct answer frame creation step
S5: correct answer frame storage step

What is claimed is:

1. An image processing apparatus comprising:
a processor configured to
select a reference frame from a frame group including a plurality of images;
acquire a reference correct answer frame representing a region of interest in the selected reference frame;
generate a complementary correct answer frame corresponding to a frame other than the reference frame included in the frame group based on at least one reference correct answer frame; and
generate a correct answer image group for machine learning from the reference correct answer frame and the complementary correct answer frame,
wherein the complementary correct answer frame is created by utilizing a shape model or a shape change model that approximates a lesion area in the reference correct answer frame.

2. The image processing apparatus according to claim 1, wherein the processor configured to select the reference frame based on a result of analysis of the plurality of images in the frame group.

3. The image processing apparatus according to claim 2, wherein the plurality of images in the frame group includes a plurality of images in time series.

4. The image processing apparatus according to claim 2, wherein the processor configured to select the reference frame based on a degree of shake or blurriness of each of the plurality of images included in the frame group.

5. The image processing apparatus according to claim 2, wherein the processor configured to select the reference frame based on a result of detection of an image feature of each of the plurality of images included in the frame group.

6. The image processing apparatus according to claim 2, wherein the processor configured to select the reference frame based on data that is detected by a gyroscope or an acceleration sensor in a case of imaging each of the plurality of images included in the frame group.

7. The image processing apparatus according to claim 2, wherein the processor configured to
receive an operation input from an interface; and
generate the reference correct answer frame by specifying the region of interest and performing the image processing on the region of interest based on the operation input.

8. The image processing apparatus according to claim 1, wherein the plurality of images in the frame group includes a plurality of images in time series.

9. The image processing apparatus according to claim 8, wherein the processor configured to select the reference frame based on a degree of shake or blurriness of each of the plurality of images included in the frame group.

10. The image processing apparatus according to claim 8, wherein the processor configured to select the reference frame based on a result of detection of an image feature of each of the plurality of images included in the frame group.

11. The image processing apparatus according to claim 8, wherein the processor configured to select the reference frame based on data that is detected by a gyroscope or an acceleration sensor in a case of imaging each of the plurality of images included in the frame group.

12. The image processing apparatus according to claim 1, wherein the processor configured to select the reference frame based on a degree of shake or blurriness of each of the plurality of images included in the frame group.

13. The image processing apparatus according to claim 12,
wherein the processor configured to quantify the degree of shake or blurriness by performing image analysis or frequency analysis on each of the plurality of images included in the frame group.

14. The image processing apparatus according to claim 12,
wherein the processor configured to quantify the degree of shake or blurriness by analyzing velocity vectors of deviation amounts or directions of the plurality of images included in the frame group.

15. The image processing apparatus according to claim 1,
wherein the processor configured to select the reference frame based on a result of detection of an image feature of each of the plurality of images included in the frame group.

16. The image processing apparatus according to claim 1,
wherein the processor configured to select the reference frame based on data that is detected by a gyroscope or an acceleration sensor in a case of imaging each of the plurality of images included in the frame group.

17. The image processing apparatus according to claim 1,
wherein the processor configured to
receive an operation input from an interface; and
generate the reference correct answer frame by specifying the region of interest and performing the image processing on the region of interest based on the operation input.

18. The image processing apparatus according to claim 1,
wherein the processor configured to, in a case where a plurality of the reference frames is selected, generate the complementary correct answer frame by performing a morphing process based on images of the regions of interest of two reference correct answer frames to an intermediate frame constituting a motion picture between the two correct answer reference frames.

19. A learned model generated by performing machine learning using a correct answer image group created by the image processing apparatus according to claim 1.

20. The learned model according to claim 19,
wherein the learned model has a configuration of a convolutional neural network.

* * * * *